United States Patent
Naruse

(10) Patent No.: US 10,849,570 B2
(45) Date of Patent: Dec. 1, 2020

(54) DETECTION APPARATUS, DETECTION METHOD, AND PROGRAM

(71) Applicant: SONY MOBILE COMMUNICATIONS INC., Tokyo (JP)

(72) Inventor: Tetsuya Naruse, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/451,578

(22) Filed: Mar. 7, 2017

(65) Prior Publication Data
US 2017/0290552 A1 Oct. 12, 2017

(51) Int. Cl.
| | |
|---|---|
| A61B 5/00 | (2006.01) |
| A61B 5/0205 | (2006.01) |
| A61B 5/0404 | (2006.01) |
| A61B 5/0408 | (2006.01) |
| A61B 5/024 | (2006.01) |
| A61B 5/0255 | (2006.01) |

(52) U.S. Cl.
CPC .......... *A61B 5/7285* (2013.01); *A61B 5/0205* (2013.01); *A61B 5/0404* (2013.01); *A61B 5/04085* (2013.01); *A61B 5/681* (2013.01); *A61B 5/7207* (2013.01); *A61B 5/7257* (2013.01); *A61B 5/7278* (2013.01); *A61B 5/742* (2013.01); *A61B 5/0255* (2013.01); *A61B 5/02427* (2013.01); *A61B 5/02438* (2013.01); *A61B 2560/0468* (2013.01); *A61B 2562/0209* (2013.01)

(58) Field of Classification Search
CPC ... A61B 5/0245; A61B 5/7285; A61B 5/0205; A61B 5/0404; A61B 5/04085; A61B 5/681; A61B 5/7207; A61B 5/7257; A61B 5/7278; A61B 5/742
See application file for complete search history.

(56) References Cited

U.S. PATENT DOCUMENTS

| | | | | |
|---|---|---|---|---|
| 7,621,876 B2 * | 11/2009 | Hoctor | ............... | A61B 5/02125 600/437 |
| 9,326,694 B2 * | 5/2016 | Cho | ................... | G06F 19/3418 |
| 2003/0216658 A1 * | 11/2003 | Ikenoue | ............... | A61B 5/0285 600/511 |
| 2008/0039731 A1 * | 2/2008 | McCombie | ........ | A61B 5/02125 600/485 |
| 2009/0143655 A1 * | 6/2009 | Shani | ................... | A61B 5/0059 600/323 |

(Continued)

FOREIGN PATENT DOCUMENTS

| | | |
|---|---|---|
| JP | H10-258039 A | 9/1998 |
| JP | 2003-135434 A | 5/2003 |

(Continued)

*Primary Examiner* — John R Downey
(74) *Attorney, Agent, or Firm* — Xsensus LLP

(57) ABSTRACT

There is provided a detection apparatus including: a heartbeat sensor that includes a plurality of electrodes and is configured to detect a first detection signal indicating heartbeat of a detection target via the plurality of electrodes; a pulse wave sensor configured to detect a second detection signal indicating a pulse wave of the detection target; and a processing unit configured to detect a pulse of the detection target on the basis of the first detection signal and the second detection signal.

17 Claims, 9 Drawing Sheets

(56) References Cited

U.S. PATENT DOCUMENTS

| | | | |
|---|---|---|---|
| 2009/0182205 A1* | 7/2009 | Cho | A61B 5/0404 600/301 |
| 2013/0267859 A1* | 10/2013 | Okuda | A61B 5/0245 600/500 |
| 2013/0310659 A1* | 11/2013 | Kawachi | A61B 5/0404 600/301 |
| 2015/0366473 A1* | 12/2015 | Shimuta | A61B 5/0245 600/479 |
| 2016/0287095 A1* | 10/2016 | Gu | A61B 5/0245 |

FOREIGN PATENT DOCUMENTS

| | | |
|---|---|---|
| JP | 2008-73462 | 4/2008 |
| JP | 2012-20063 A | 2/2012 |
| JP | 2012-71018 A | 4/2012 |
| JP | 2013-230291 A | 11/2013 |

* cited by examiner

DETECTION APPARATUS, DETECTION METHOD, AND PROGRAM

CROSS REFERENCE TO RELATED APPLICATIONS

This application claims the benefit of Japanese Priority Patent Application JP 2016-079495 filed Apr. 12, 2016, the entire contents of which are incorporated herein by reference.

BACKGROUND

The present disclosure relates to a detection apparatus, a detection method, and a program.

Technologies related to an apparatus that includes a sensor capable of detecting a signal concerned with heartbeat have been developed. An example of the sensor capable of detecting a signal concerned with heartbeat is a heartbeat sensor that detects a signal indicating heartbeat according to a potential difference between a plurality of electrodes. An example of technologies related to an apparatus including a heartbeat sensor is the technology described in JP 2008-73462A.

SUMMARY

A signal indicating heartbeat, such as an electrocardiogram waveform (hereinafter, referred to as an "electrocardiogram (ECG)" in some cases), can be detected by using a heartbeat sensor. However, since the heartbeat sensor detects a signal indicating heartbeat according to a potential difference between a plurality of electrodes, a living body serving as a detection target (hereinafter, simply referred to as a "detection target") needs to be touching the plurality of electrodes in order that a signal indicating heartbeat is detected by using the heartbeat sensor.

Therefore, detection of heartbeat using the heartbeat sensor is suitable for the purpose of detecting heartbeat temporarily, but, in terms of convenience of the detection target, is not suitable for the purpose of detecting heartbeat continuously when the detection target is walking, for example.

Another example of a sensor capable of detecting a signal concerned with heartbeat is a pulse wave sensor that optically detects a pulse wave using a method called photoplethysmography (hereinafter, referred to as "PPG" in some cases). A pulse wave is a volumetric change in the blood vessel that accompanies pulsation of the heart of a living body. Therefore, the number of pulses (hereinafter, referred to as a "pulse rate") that is detected from a pulse wave detected by a pulse wave sensor in a certain period coincides with the number of heartbeats (hereinafter, referred to as a "heart rate") detected by a heartbeat sensor in the certain period.

A pulse wave sensor irradiates a living body serving as a detection target (hereinafter, simply referred to as a "detection target") with light from a light source, such as a light-emitting diode (LED), and obtains a signal indicating the intensity of light reflected from the detection target by a light-receiving element, such as a photodiode (photo detector), thereby detecting a pulse wave of the detection target. Hemoglobin in the blood flowing through the blood vessel of the detection target has a property of absorbing light; therefore, a pulse wave of the detection target is detected by observing reflected light by the photodiode. Hence, detection of a pulse wave using the pulse wave sensor is more suitable for the purpose of detecting a pulse continuously when the detection target is walking, for example, than detection of heartbeat using the heartbeat sensor is.

However, a signal that is detected in a pulse wave sensor changes wildly. Therefore, in the case where a pulse of a detection target is detected by using a signal detected by the pulse wave sensor, the pulse is detected by frequency analysis of the signal detected by the pulse wave sensor. In addition, a pulse rate of the detection target is estimated from the periodicity of the detected pulse. Therefore, in the case where the pulse rate is estimated on the basis of the signal detected by the pulse wave sensor, it may take approximately several tens of seconds until the pulse rate of the detection target is obtained. Hence, in the case where the pulse rate is estimated on the basis of the signal detected by the pulse wave sensor, it may take several tens of seconds or more until a state where the detection target is able to check the pulse rate is reached after measurement by the pulse wave sensor is started.

The present disclosure proposes a novel and improved detection apparatus, detection method, and program that are capable of shortening time taken for detection of a pulse of a detection target.

According to an embodiment of the present disclosure, there is provided a detection apparatus including: a heartbeat sensor that includes a plurality of electrodes and is configured to detect a first detection signal indicating heartbeat of a detection target via the plurality of electrodes; a pulse wave sensor configured to detect a second detection signal indicating a pulse wave of the detection target; and a processing unit configured to detect a pulse of the detection target on the basis of the first detection signal and the second detection signal.

According to an embodiment of the present disclosure, there is provided a detection method executed by a detection apparatus, including: detecting a pulse of a detection target, on the basis of a first detection signal that is acquired from a heartbeat sensor including a plurality of electrodes and indicates heartbeat of the detection target, and a second detection signal that is acquired from a pulse wave sensor and indicates a pulse wave of the detection target.

According to an embodiment of the present disclosure, there is provided a program causing a computer to implement a function of: detecting a pulse of a detection target, on the basis of a first detection signal that is acquired from a heartbeat sensor including a plurality of electrodes and indicates heartbeat of the detection target, and a second detection signal that is acquired from a pulse wave sensor and indicates a pulse wave of the detection target.

According to an embodiment of the present disclosure, time taken for detection of a pulse of a detection target can be shortened.

Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
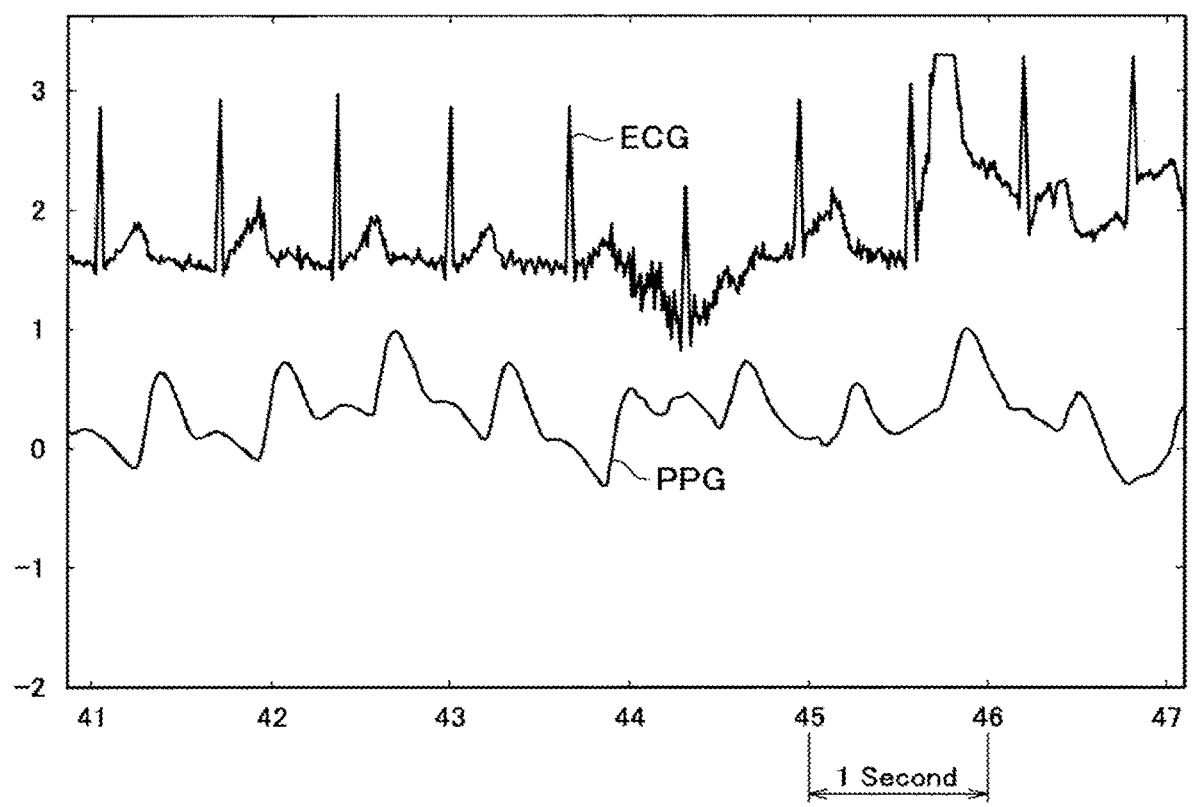
FIG. 1 is an explanatory diagram illustrating examples of a first detection signal and a second detection signal according to the embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.
1. Detection method according to present embodiment
2. Detection apparatus according to present embodiment
3. Program according to present embodiment
(Detection Method According to Present Embodiment)

First, a detection method according to the present embodiment will be described. As an example, a case where processing related to the detection method according to the present embodiment is performed by a detection apparatus according to the present embodiment will be described.
[1] Overview of Detection Method According to Present Embodiment As described above, in terms of convenience of the detection target, detection of heartbeat using the heartbeat sensor is not suitable for the purpose of detecting heartbeat continuously when the detection target is walking, for example.

In contrast, detection of a pulse wave using the pulse wave sensor is more suitable for the purpose of detecting a pulse continuously when the detection target is walking, for example, than detection of heartbeat using the heartbeat sensor is. However, as described above, it may take several tens of seconds or more until a state where the detection target is able to check the pulse rate is reached after measurement by the pulse wave sensor is started.

Hence, the detection apparatus according to the present embodiment detects a pulse of a detection target on the basis of a signal indicating heartbeat of the detection target (hereinafter, referred to as a "first detection signal") acquired from a heartbeat sensor and a signal indicating a pulse wave of the detection target (hereinafter, referred to as a "second detection signal") acquired from a pulse wave sensor. In the following description, processing of detecting a pulse of the detection target according to the present embodiment is referred to as "detection processing".

For example, the detection apparatus according to the present embodiment acquires the first detection signal from a heartbeat sensor included in the detection apparatus according to the present embodiment, or an external heartbeat sensor connected to the detection apparatus according to the present embodiment. For example, the detection apparatus according to the present embodiment acquires the second detection signal from a pulse wave sensor included in the detection apparatus according to the present embodiment, or an external pulse wave sensor connected to the detection apparatus according to the present embodiment.

FIG. 1 is an explanatory diagram illustrating examples of the first detection signal and the second detection signal according to the present embodiment. A waveform "ECG" in FIG. 1 illustrates an example of an electrocardiogram waveform indicated by the first detection signal. A waveform "PPG" in FIG. 1 illustrates an example of a waveform of a pulse wave indicated by the second detection signal.

As described above, a pulse wave is a volumetric change in the blood vessel that accompanies pulsation of the heart of a living body. Therefore, heartbeat detected on the basis of the first detection signal and a pulse detected on the basis of the second detection signal have a one-to-one correspondence, and the heartbeat in the electrocardiogram waveform appears in the electrocardiogram waveform earlier than the pulse in the waveform of the pulse wave. The heartbeat is detected by detection of peak positions in the electrocardiogram waveform, and peak positions in the electrocardiogram waveform are clearer than peak positions in the waveform of the pulse wave, as illustrated in FIG. 1.

Hence, the detection apparatus according to the present embodiment uses heartbeat detected on the basis of the first detection signal as an index to detect a pulse of the detection target from the second detection signal.

Using heartbeat detected on the basis of the first detection signal as an index to detect a pulse of the detection target from the second detection signal, as described above, enables the pulse of the detection target to be detected more easily from the second detection signal.

Accordingly, the detection apparatus according to the present embodiment performs the detection processing as the processing related to the detection method according to the present embodiment, which shortens time taken for detection of a pulse of the detection target.

In addition, as described above, a pulse rate of the detection target is estimated from the periodicity of the detected pulse; therefore, when time taken for detection of a pulse of the detection target is shortened, time taken until the pulse rate is estimated after measurement by the pulse wave sensor is started is also shortened. Accordingly, performing the detection processing as the processing related to the detection method according to the present embodiment further shortens "time taken until a state where the detection target is able to check the pulse rate is reached after measurement by the pulse wave sensor is started", which improves the convenience of the detection target.

Furthermore, since heartbeat is used as an index in the detection processing, continuous detection of heartbeat by the heartbeat sensor need not be performed, as long as heartbeat serving as an index is detected from the first detection signal. In other words, in the case where the detection processing is performed as the processing related to the detection method according to the present embodiment, detection of a pulse is enabled by using the heartbeat sensor for "the purpose of detecting heartbeat temporarily", for which detection of heartbeat using the heartbeat sensor is suitable. Hence, in the case where the detection processing is performed as the processing related to the detection method according to the present embodiment, there is no fear of impairing the convenience of the detection target, unlike in the case where heartbeat is continuously detected by using a heartbeat sensor.

[2] Processing Related to Detection Method According to Present Embodiment

Next, the processing related to the detection method according to the present embodiment will be described more specifically.

[2-1] Example of Detection Apparatus According to Present Embodiment

Figure 2:
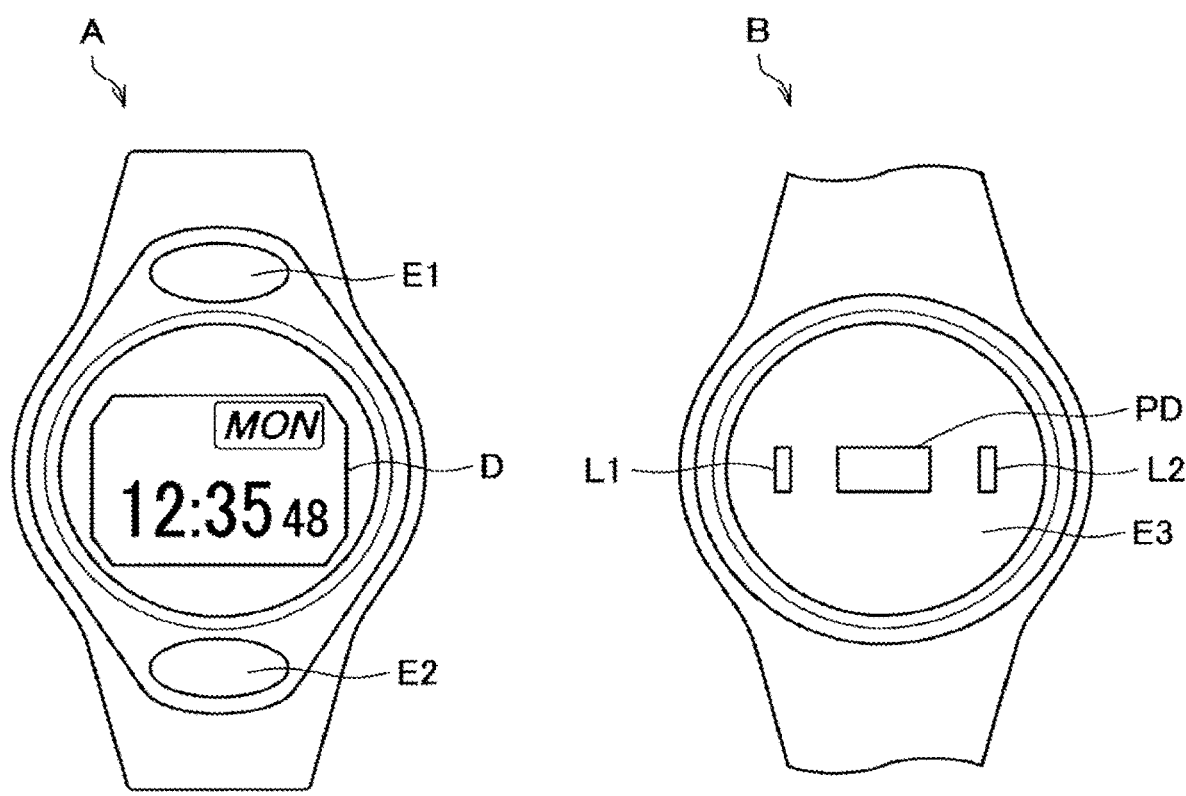
FIG. 2 is an explanatory diagram illustrating an example of a detection apparatus according to the embodiment.

FIG. 2 is an explanatory diagram illustrating an example of the detection apparatus according to the present embodiment. FIG. 2 illustrates an example of the detection apparatus according to the present embodiment when the detection apparatus according to the present embodiment is applied to a clock-type wearable apparatus that is worn on the detection target's arm to be used. A of FIG. 2 illustrates a surface on the opposite side to a surface to be worn on the detection target's arm in the detection apparatus according to the present embodiment, and B of FIG. 2 illustrates a surface on the side to be worn on the detection target's arm in the detection apparatus according to the present embodiment.

The detection apparatus according to the present embodiment includes, for example, electrodes E1, E2, and E3, a display device D, light sources L1 and L2, and a photodiode PD.

The electrodes E1, E2, and E3 are a plurality of electrodes constituting a heartbeat sensor. In the heartbeat sensor, the first detection signal indicating heartbeat is detected according to a potential difference between electrodes, which occurs when the detection target touches at least two of the electrodes E1, E2, and E3. The number of electrodes included in the detection apparatus according to the present embodiment is not limited to three as illustrated in FIG. 2, and the detection apparatus according to the present embodiment may include, for example, two or four or more electrodes.

For example, in the example illustrated in FIG. 2, the electrode E3 is provided on the surface on the side to be worn on the detection target's arm in the detection apparatus according to the present embodiment; therefore, in a state where the detection target is wearing the detection apparatus according to the present embodiment, a state where the detection target is touching the electrode E3 is maintained. Consequently, when the detection target wearing the detection apparatus according to the present embodiment touches at least one of the electrodes E1 and E2, the first detection signal is detected in the heartbeat sensor.

The display device D displays either or both of text and an image. On a display screen of the display device D, contents based on a result of the detection processing (e.g., the pulse rate of the detection target), time, a user interface (UI), and the like are displayed, for example. Note that the detection apparatus according to the present embodiment may have a configuration without the display device D.

The light sources L1 and L2 and the photodiode PD constitute a pulse wave sensor. Examples of the light sources L1 and L2 are LEDs that emit red light, green light, and the like.

For example, in the example illustrated in FIG. 2, the light sources L1 and L2 and the photodiode PD are provided on the surface on the side to be worn on the detection target's arm in the detection apparatus according to the present embodiment; therefore, in a state where the detection target is wearing the detection apparatus according to the present embodiment, a state where the pulse wave sensor is able to detect a pulse wave is maintained.

As illustrated in FIG. 2, for example, the detection apparatus according to the present embodiment includes the heartbeat sensor and the pulse wave sensor.

Here, in the detection apparatus according to the present embodiment, detection of the first detection signal in the heartbeat sensor may be performed in conjunction with detection of the second detection signal in the pulse wave sensor.

For example, making the plurality of electrodes of the heartbeat sensor function as switches for detection start in the pulse wave sensor enables detection in the heartbeat sensor to be performed in conjunction with detection in the pulse wave sensor.

In the detection apparatus according to the present embodiment illustrated in FIG. 2, for example, the electrodes E1 and E2 function as switches for detection start in the pulse wave sensor. In the case where the electrodes E1 and E2 function as switches for detection start in the pulse wave sensor, the detection target wearing the detection apparatus according to the present embodiment can cause detection by the heartbeat sensor and detection by the pulse wave sensor to be started by touching the electrode E1 or the electrode E2.

A case where the detection apparatus according to the present embodiment illustrated in FIG. 2 performs the processing related to the detection method according to the present embodiment will be described as an example. Note that a device to which the detection apparatus according to the present embodiment is applicable is not limited to a clock-type wearable apparatus as illustrated in FIG. 2. Application examples of the detection apparatus according to the present embodiment will be described later.

[2-2] Example of Processing Related to Detection Method According to Present Embodiment As described above, the detection apparatus according to the present embodiment performs "detection processing of detecting a pulse of the detection target on the basis of the first detection signal and the second detection signal".

Figure 3:
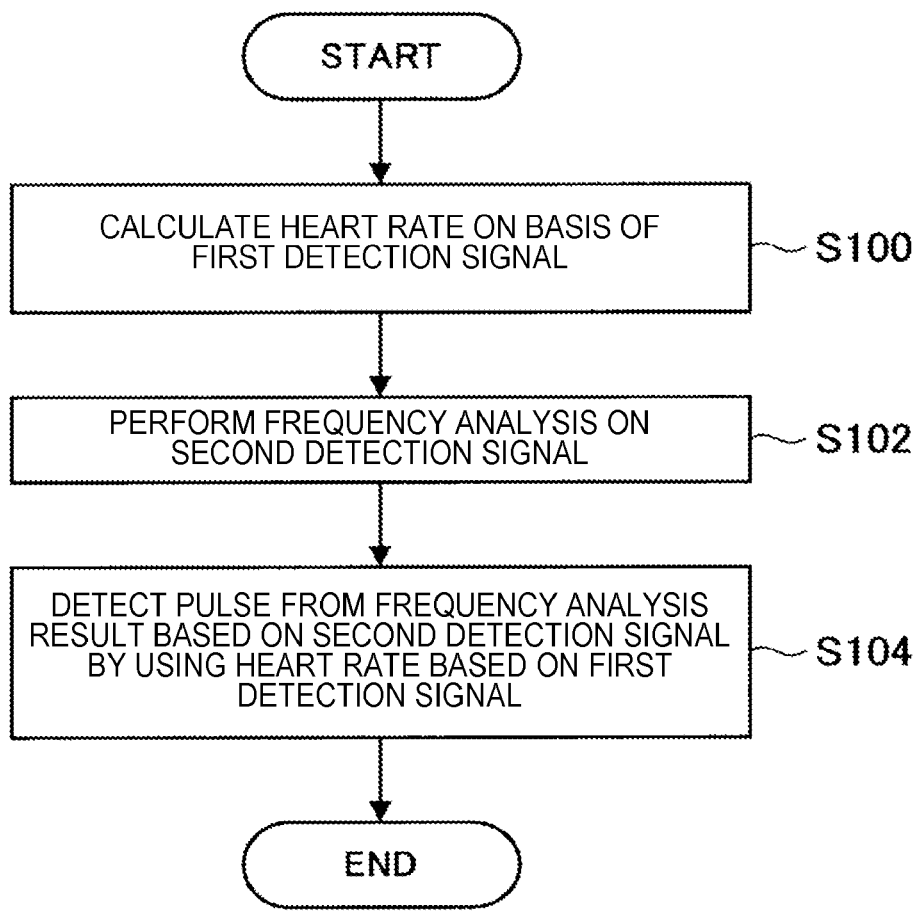
FIG. 3 is a flowchart illustrating an example of processing related to a detection method according to the embodiment.
Figure 4:
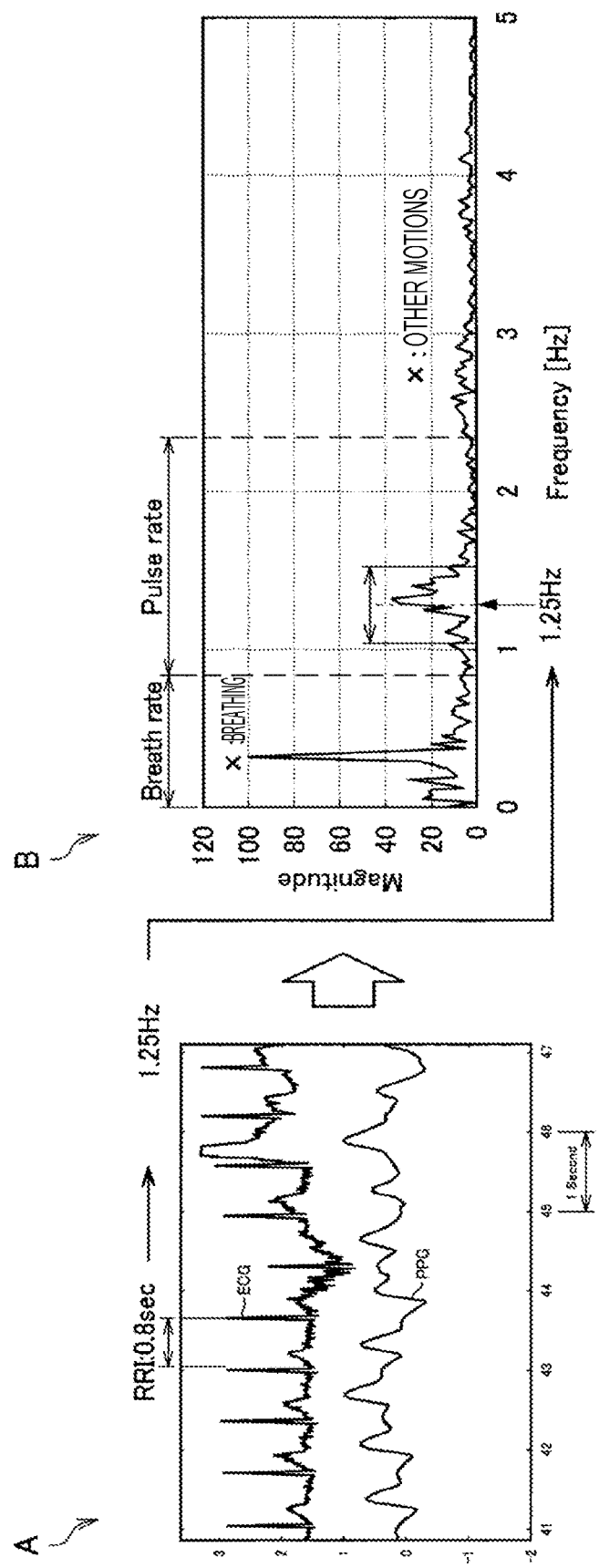
FIG. 4 is an explanatory diagram for describing an example of processing related to a detection method according to the embodiment.
Figure 5:
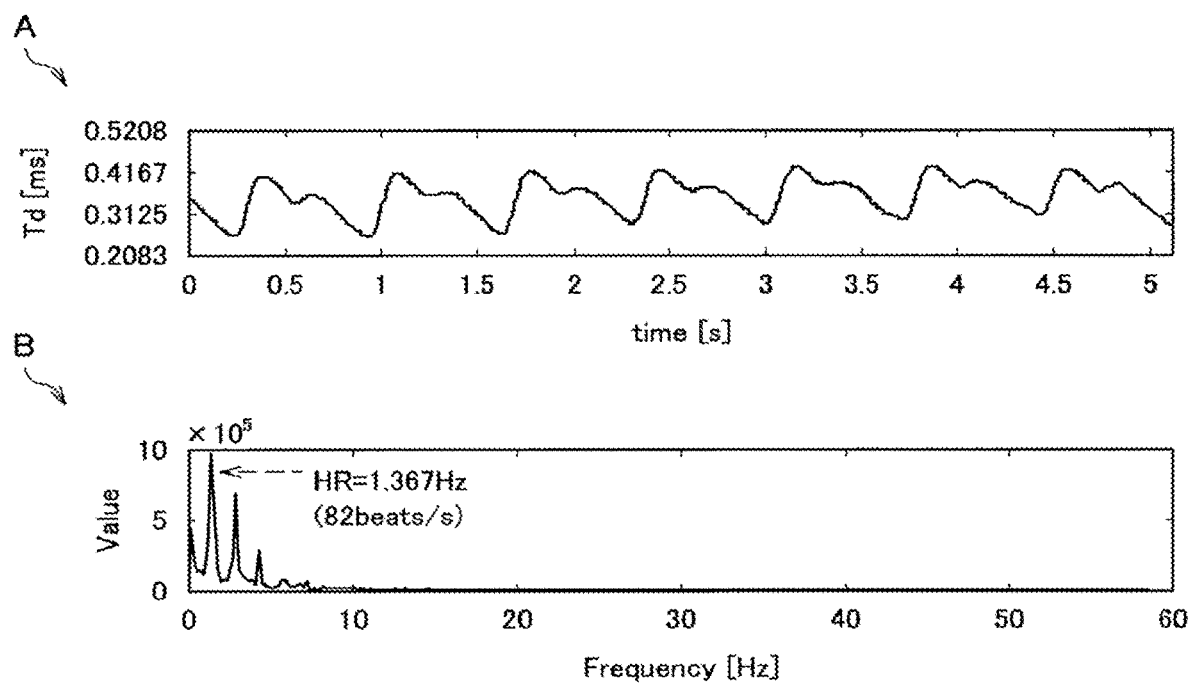
FIG. 5 is an explanatory diagram for describing an example of processing related to a detection method according to the embodiment.

FIG. 3 is a flowchart illustrating an example of the processing related to the detection method according to the present embodiment, and illustrates an example of the detection processing. FIGS. 4 and 5 are explanatory diagrams for describing the example of the processing related to the detection method according to the present embodiment. Hereinafter, the example of the detection processing will be described referring to FIGS. 3 to 5 as appropriate.

The detection apparatus according to the present embodiment calculates a heart rate on the basis of the first detection signal (S100).

For example, the detection apparatus according to the present embodiment detects a heartbeat interval (hereinafter, referred to as a "R R interval (RRI)") from the first detection signal. The RRI can be obtained by detecting an interval between peak positions in the first detection signal, as illustrated in A of FIG. 4, for example.

Moreover, the detection apparatus according to the present embodiment performs a computation in Expression 1 below, for example, thereby calculating a heart rate in a predetermined period. Here, Expression 1 below is an example of a computation when a heart rate for one minute (an example of the predetermined period) is calculated. In other words, the unit of the heart rate calculated according to Expression 1 below is "[beats per minute]". In Expression 1 below, the RRI is expressed by "[sec]". Note that the predetermined period according to the present embodiment is not limited to one minute, and may be any period.

$$\text{Heart rate}=1/RRI\times 60 \qquad \text{(Expression 1)}$$

The detection apparatus according to the present embodiment performs frequency analysis on the second detection signal (S102).

FIG. 3 illustrates an example in which the processing of step S102 is performed after the processing of step S100 is performed, but the detection apparatus according to the present embodiment can perform the processing of step S100 and the processing of step S102 in parallel, for example. The processing of step S102 is performed continuously until detection of the pulse wave of the detection target ends, for example.

The detection apparatus according to the present embodiment performs the frequency analysis by performing fast Fourier transform (hereinafter, referred to as "FFT" in some cases) on the second detection signal. The FFT performed on the second detection signal converts the second detection signal from a time domain as illustrated in A of FIG. 5 to a frequency domain as illustrated in B of FIG. 5.

Here, as illustrated in FIG. 5, peak positions are clearer in the frequency domain than in the time domain. Hence, performing frequency analysis on the second detection signal in step S102 enables detection of a pulse from the second detection signal to be performed more easily.

Using the heart rate based on the first detection signal calculated in step S100, the detection apparatus according to the present embodiment detects a pulse from a result of the frequency analysis based on the second detection signal (S104).

The detection apparatus according to the present embodiment performs a calculation in Expression 2 below, for example, thereby calculating a frequency of heartbeat (a cycle of heartbeat) from the heart rate calculated in step S100. Here, Expression 2 below is an example of a computation when the frequency of the heartbeat is calculated on the basis of the heart rate calculated in Expression 1 above. The unit of the frequency of the heartbeat in Expression 2 below is expressed by "[Hz]".

$$\text{Frequency of heartbeat}=\text{heart rate}/60 \qquad \text{(Expression 2)}$$

In the first detection signal illustrated in A of FIG. 4, for example, the RRI is 0.8 [sec]; thus, according to Expressions 1 and 2 above, the frequency of the heartbeat is 1.25 [Hz]. Note that the detection apparatus according to the present embodiment can also calculate the frequency of the heartbeat on the basis of the RRI detected from the first detection signal, without performing the processing of step S100, that is, without calculating the heart rate.

The detection apparatus according to the present embodiment detects a pulse of the detection target from a result of the frequency analysis in step S102, on the basis of the calculated frequency of the heartbeat. The detection apparatus according to the present embodiment uses the frequency of the heartbeat calculated according to Expression 2, for example, as an index for detecting the pulse of the detection target from the second detection signal, thereby detecting the pulse of the detection target from the result of the frequency analysis in step S102.

In FIG. 4, for example, 1.25 [Hz] is obtained as the frequency of the heartbeat on the basis of the first detection signal illustrated in A of FIG. 4. The detection apparatus according to the present embodiment detects a peak value within a predetermined frequency range including 1.25 [Hz], which is the calculated frequency of the heartbeat, from a result of the frequency analysis performed on the second detection signal, illustrated in B of FIG. 4. An example of the predetermined frequency range is "a range between a frequency obtained by subtracting a set value of an error from the calculated frequency of the heartbeat and a frequency obtained by adding the value of the error to the frequency of the heartbeat". The value of the error may be a fixed value set in advance, or may be a variable value that can be changed on the basis of operation by a user of the detection apparatus according to the present embodiment, for example.

Then, the detection apparatus according to the present embodiment specifies a frequency corresponding to the detected peak value as a frequency of a pulse (a cycle of a pulse), for example, thereby detecting the pulse of the detection target from the result of the frequency analysis in step S102. By detecting the pulse of the detection target in the above manner, the detection apparatus according to the present embodiment can detect the pulse of the detection target even in the case where there is a change in the second detection signal due to breathing of the detection target, other motions in the detection target, and the like, as illustrated in B of FIG. 4, for example.

Furthermore, the detection apparatus according to the present embodiment may calculate a pulse rate of the detection target on the basis of the detected pulse of the detection target. Here, processing related to the calculation of the pulse rate of the detection target based on the detected pulse of the detection target corresponds to processing related to estimation of the pulse rate of the detection target. For example, the detection apparatus according to the present embodiment calculates a pulse rate in a predetermined period on the basis of the specified frequency of the pulse.

More specifically, the detection apparatus according to the present embodiment substitutes a value of the frequency of the pulse specified as the value of "1/RRI" into Expression 1 above, for example, thereby calculating the pulse rate.

The detection apparatus according to the present embodiment performs the processing illustrated in FIG. 3, for example, as the detection processing. In the case where the processing illustrated in FIG. 3 is performed, for example, the detection apparatus according to the present embodiment can use heartbeat detected on the basis of the first detection signal as an index to detect a pulse of the detection target from the second detection signal.

Hence, the detection apparatus according to the present embodiment performs the processing illustrated in FIG. 3, for example, which shortens time taken for detection of a pulse of the detection target.

In addition, the detection apparatus according to the present embodiment can improve detection precision of the pulse of the detection target by performing the detection processing, because the pulse of the detection target can be detected even in the case where there is a change in the second detection signal due to breathing of the detection target, other motions in the detection target, and the like.

Furthermore, by performing the processing illustrated in FIG. 3, for example, the detection apparatus according to the present embodiment can have an effect obtained by performing the detection processing described above.

The detection processing related to the detection method according to the present embodiment is not limited to the example illustrated in FIG. 3.

For example, when the pulse of the detection target is detected on the basis of the frequency of the heartbeat in step S104 of FIG. 3, the detection apparatus according to the present embodiment can detect a pulse of the detection target from a result of frequency analysis, on the basis of a frequency corresponding to the pulse detected on the basis of the frequency of the heartbeat.

The detection apparatus according to the present embodiment uses a frequency corresponding to the pulse detected on the basis of the frequency of the heartbeat as a new index to detect a pulse of the detection target from the second detection signal. As in the case of using the frequency of the heartbeat as an index, for example, the detection apparatus according to the present embodiment detects a pulse of the detection target by detecting a peak value within a predetermined frequency range including "a frequency corresponding to the pulse detected on the basis of the frequency of the heartbeat".

In addition, when a pulse of the detection target is newly detected on the basis of "a frequency corresponding to the pulse detected on the basis of the frequency of the heartbeat", for example, the detection apparatus according to the present embodiment detects a pulse of the detection target from a result of frequency analysis, on the basis of a frequency corresponding to the newly detected pulse.

In other words, the detection apparatus according to the present embodiment can use a frequency corresponding to the last detected pulse, for example, as a new index to detect a pulse of the detection target from the second detection signal. Using a frequency corresponding to the last detected pulse as a new index enables a pulse of the detection target to be detected more accurately from the second detection signal.

In addition, each time a pulse is newly detected, the detection apparatus according to the present embodiment may calculate a pulse rate in a predetermined period on the basis of a frequency of the detected pulse. Using, each time a pulse is newly detected, a frequency of the detected pulse as a new index enables a pulse rate of the detection target to be calculated more accurately.

Figure 6:
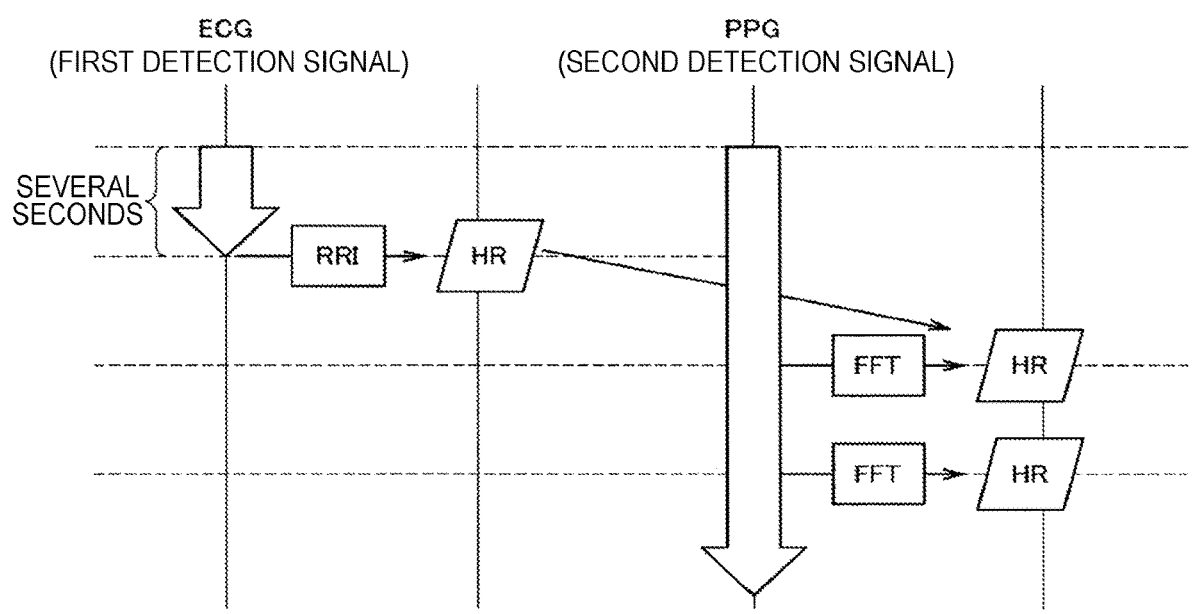
FIG. 6 is an explanatory diagram for describing an example of processing related to a detection method according to the embodiment.

FIG. 6 is an explanatory diagram for describing an example of the processing related to the detection method according to the present embodiment, and illustrates an overview of acquisition of a pulse rate, which is enabled by the detection processing. In FIG. 6, a heart rate acquired on the basis of the first detection signal and a pulse rate acquired on the basis of the second detection signal are both referred to as a "heart rate (HR)" for convenience.

The detection apparatus according to the present embodiment calculates a heart rate on the basis of the first detection signal. Then, the detection apparatus according to the present embodiment uses a frequency of heartbeat calculated from the calculated heart rate as an index to detect a pulse wave from a result of frequency conversion of the second detection signal, and obtains a pulse rate in a predetermined period from a frequency of the detected pulse wave.

Moreover, the detection apparatus according to the present embodiment uses the frequency of the detected pulse wave as an index to detect a pulse wave from a result of frequency conversion of the second detection signal, and obtains a pulse rate in a predetermined period from a frequency of the detected pulse wave.

Performing the processing illustrated in FIG. 6, for example, in the detection apparatus according to the present embodiment, enables a pulse rate to be continuously acquired while detection of the second detection signal by the pulse wave sensor is continued.

In addition, in the case of detecting a pulse wave from the second detection signal, when a detection result of a motion of the detection target is obtained, the detection apparatus according to the present embodiment may detect a pulse wave, excluding a motion component of the detection target indicated by the detection result of the motion of the detection target. The motion of the detection target is acquired from, for example, a motion sensor included in the detection apparatus according to the present embodiment, or a motion sensor connected to the detection apparatus according to the present embodiment. As the motion sensor, one or more sensors capable of detecting a motion, such as an acceleration sensor and an angular velocity sensor, may be used.

By detecting a pulse wave, excluding a motion component of the detection target, the detection apparatus according to the present embodiment can improve detection precision of a pulse of the detection target.

The detection apparatus according to the present embodiment performs the detection processing as described above as the processing related to the detection method according to the present embodiment.

The processing related to the detection method according to the present embodiment is not limited to the above-described detection processing. For example, the detection apparatus according to the present embodiment can further perform either or both of processing of (I) below and processing of (II) below.

(I) Display Control Processing

The detection apparatus according to the present embodiment causes the pulse rate of the detection target calculated in the above-described detection processing, for example, to be displayed on a display screen.

Examples of the display screen on which the detection apparatus according to the present embodiment causes the pulse rate of the detection target to be displayed include a display device included in the detection apparatus according to the present embodiment, such as the display device D illustrated in FIG. 2, and a display device external to the detection apparatus according to the present embodiment. For example, the detection apparatus according to the present embodiment transmits a control signal including a display command and data indicating a pulse rate to a display device included in the detection apparatus according to the present embodiment, or an external display device, thereby causing the calculated pulse rate of the detection target to be displayed on the display screen.

By causing the calculated pulse rate of the detection target to be displayed on the display screen, the detection apparatus according to the present embodiment enables a person who sees the display screen, such as the detection target, to visually recognize the calculated pulse rate of the detection target, for example.

(II) Recording Control Processing

The detection apparatus according to the present embodiment causes the pulse rate of the detection target calculated in the above-described detection processing, for example, to be recorded on a recording medium.

Examples of the recording medium on which the detection apparatus according to the present embodiment causes the pulse rate of the detection target to be recorded include a recording medium constituting a storage unit (described later) included in the detection apparatus according to the present embodiment, and a recording medium external to the detection apparatus according to the present embodiment. For example, the detection apparatus according to the present embodiment transmits a control signal including a recording command and data indicating a pulse rate to a recording medium constituting the storage unit (described later), or an external recording medium, thereby causing the calculated pulse rate of the detection target to be recorded on the recording medium.

By causing the calculated pulse rate of the detection target to be recorded on the recording medium, the detection apparatus according to the present embodiment enables data indicating a history of calculated pulse rates of the detection target to be stored in the recording medium, for example.

[2-3] Example of Processing of Detection Apparatus According to Present Embodiment in Use Case in which Detection Apparatus According to Present Embodiment is Used Next, an example of processing of the detection apparatus according to the present embodiment in a use case in which the detection apparatus according to the present embodiment is used will be described. Hereinafter, a use case in which a pulse rate is measured by using the detection apparatus according to the present embodiment in the case where a user (an example of the detection target) wearing the detection apparatus according to the present embodiment does exercise will be used as an example to describe the example of the processing of the detection apparatus according to the present embodiment.

Figure 7:
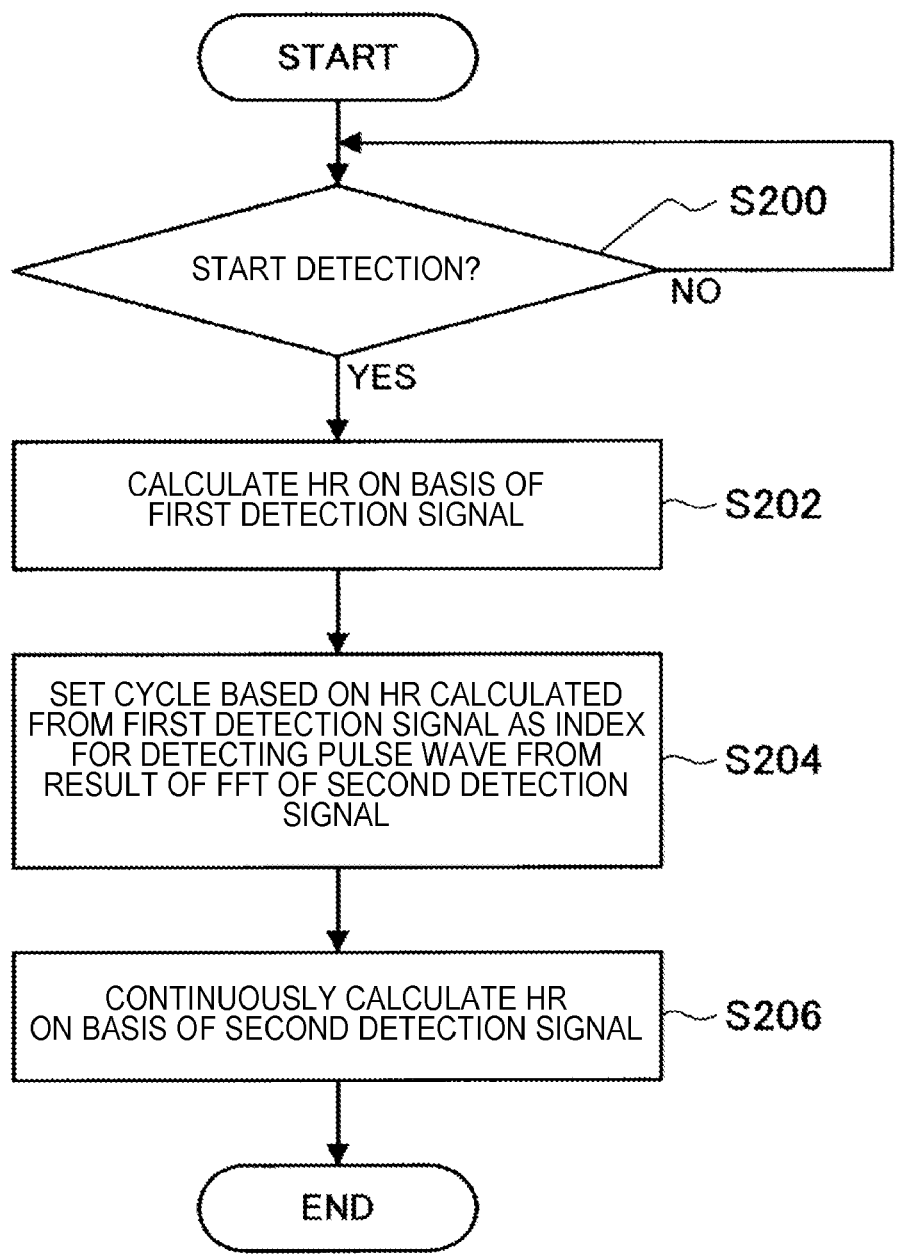
FIG. 7 is a flowchart illustrating an example of processing of a detection apparatus in a use case in which a detection apparatus according to the embodiment is used.

FIG. 7 is a flowchart illustrating the example of the processing of the detection apparatus according to the present embodiment in the use case in which the detection apparatus according to the present embodiment is used. In FIG. 7, a heart rate acquired on the basis of the first detection signal and a pulse rate acquired on the basis of the second detection signal are both referred to as a "HR", as in FIG. 6.

The detection apparatus according to the present embodiment determines whether to start detection of a pulse (S200).

For example, in the case where operation on the electrode E1 or the electrode E2 illustrated in FIG. 2, which functions as a switch for starting detection in the heartbeat sensor and the pulse wave sensor, is detected for a set period or longer (or in the case where the operation is detected for longer than the period), the detection apparatus according to the present embodiment determines to start detection of a pulse. The detection apparatus according to the present embodiment determines that the operation is being detected when, for example, a potential difference between a plurality of electrodes is being detected in the heartbeat sensor. An example of the set period is a period that allows a heart rate to be calculated on the basis of the first detection signal obtained from the heartbeat sensor, such as several seconds.

When detection of a pulse is not determined to be started in step S200, the detection apparatus according to the present embodiment refrains from proceeding with the processing until detection of a pulse is determined to be started.

When detection of a pulse is determined to be started in step S200, the detection apparatus according to the present embodiment calculates a HR on the basis of the first detection signal obtained from the heartbeat sensor, as in step S100 of FIG. 3, for example (S202).

Although not illustrated in FIG. 7, when detection of a pulse is determined to be started in step S200, the detection apparatus according to the present embodiment may notify the user that detection of a pulse is started. For example, the detection apparatus according to the present embodiment notifies the user that detection of a pulse is started by one or more of the following notification methods: a visual notification method of causing the display screen of the display device D to display text or the like, an auditory notification method of causing a sound output device (not illustrated), such as a speaker, to output sound, and a tactile notification method of causing a vibration device (not illustrated) to vibrate.

Notifying the user that detection of a pulse is started enables the user to recognize that the user is allowed to stop the operation on the electrode E1 or the electrode E2 illustrated in FIG. 2, and act freely, for example.

The detection apparatus according to the present embodiment sets a cycle (a frequency of heartbeat) based on the HR calculated from the first detection signal as an index for detecting a pulse of the detection target from a frequency analysis result of the second detection signal, as in step S104 of FIG. 3, for example (S204).

The detection apparatus according to the present embodiment continuously calculates a HR on the basis of the second detection signal, as described with reference to FIG. 6, for example (S206). In addition, the detection apparatus according to the present embodiment causes the calculated HR to be displayed on the display screen of the display device D.

At this time, the user need not be touching the electrodes E1 and E2 of the heartbeat sensor illustrated in FIG. 2, and therefore can do exercise freely. Hence, the user can cause the detection apparatus according to the present embodiment to keep calculating his/her pulse rate during exercise, as long as the user is wearing the detection apparatus according to the present embodiment and keeps the detection apparatus according to the present embodiment in a pulse measurement state.

(Detection Apparatus According to Present Embodiment)

Next, an example of a configuration of the detection apparatus according to the present embodiment, which can perform the above-described processing related to the detection method according to the present embodiment, will be described.

Figure 8:
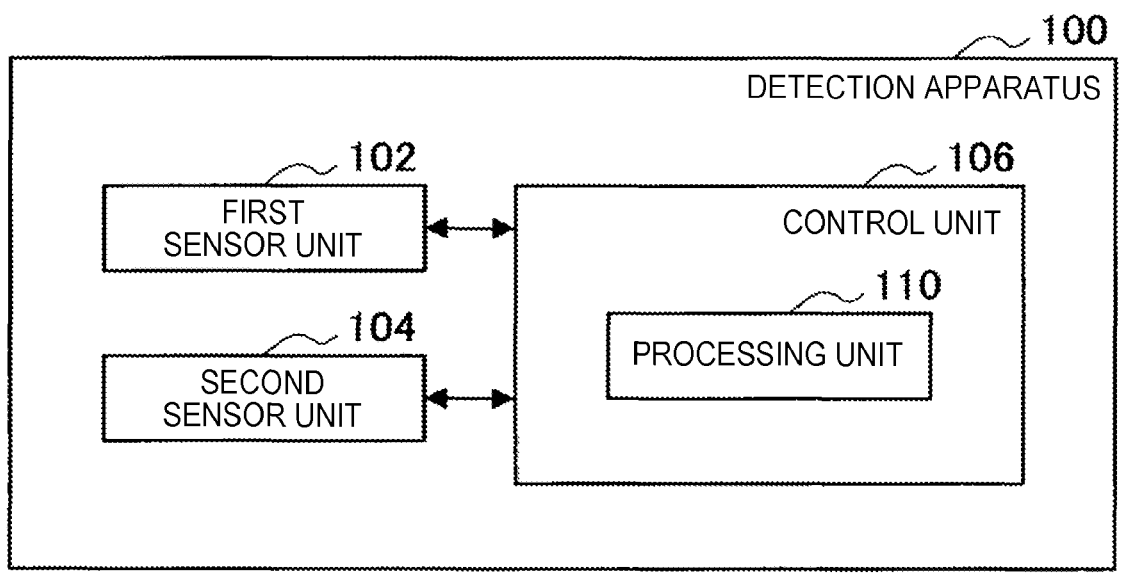
FIG. 8 is a block diagram illustrating an example of a configuration of a detection apparatus according to the embodiment.

FIG. 8 is a block diagram illustrating an example of a configuration of a detection apparatus 100 according to the present embodiment. The detection apparatus 100 includes, for example, a first sensor unit 102, a second sensor unit 104, and a control unit 106.

For example, the detection apparatus 100 may include a read only memory (ROM) (not illustrated), a random access memory (RAM) (not illustrated), a storage unit (not illustrated), an operation unit (not illustrated) that can be operated by the user of the detection apparatus 100, a display unit (not illustrated) that causes various screens to be displayed on the display screen, and the like. In the detection apparatus 100, the components are connected to one another, for example, by a bus serving as a data transmission path. For example, the detection apparatus 100 is driven by electric power supplied from an internal power source such as a battery included in the detection apparatus 100, electric power supplied from an external power source connected thereto, or the like.

The ROM (not illustrated) stores a program and control data such as operation parameters which are used by the control unit 106. The RAM (not illustrated) temporarily stores, for example, a program executed by the control unit 106.

The storage unit (not illustrated) is a storage device included in the detection apparatus 100, and stores various data of, for example, various kinds of applications. Here, examples of the storage unit (not illustrated) include a magnetic recording medium such as a hard disk (Hard Disk) and a non-volatile memory such as a flash memory. The storage unit (not illustrated) may be removably attached to the detection apparatus 100.

The operation unit (not illustrated) is an operation input device which will be described later. The display unit (not illustrated) is a display device which will be described later.

[Exemplary Hardware Configuration of Detection Apparatus 100]

Figure 9:
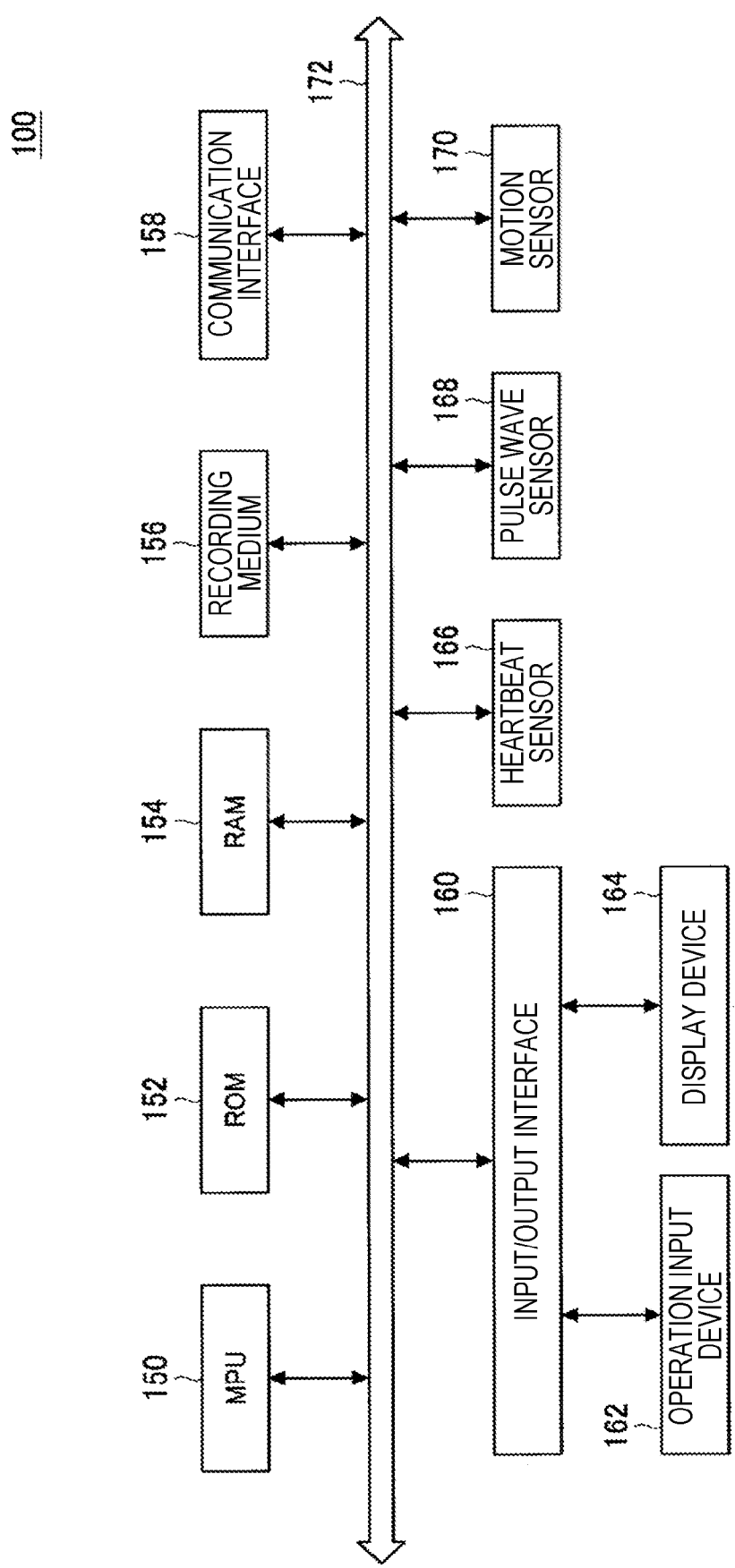
FIG. 9 is an explanatory diagram illustrating an example of a hardware configuration of a detection apparatus according to the embodiment.

FIG. 9 is an explanatory diagram illustrating an example of a hardware configuration of the detection apparatus 100 according to the present embodiment. The detection apparatus 100 includes, for example, an MPU 150, a ROM 152, a RAM 154, a recording medium 156, a communication interface 158, an input/output interface 160, an operation input device 162, a display device 164, a heartbeat sensor 166, a pulse wave sensor 168, and a motion sensor 170.

The MPU 150 is configured with, for example, one or more processors configured with an operation circuit such as a micro processing unit (MPU), various kinds of processing circuits, and the like and functions as the control unit 106 that controls the detection apparatus 100 in general. The MPU 150 undertakes, for example, the role of a processing unit 110 (which will be described later) in the detection apparatus 100. The processing unit 110 may be configured with a dedicated (or general-purpose) circuit (for example, a processor separate from the MPU 150 or the like) capable of performing processing of the processing unit 110.

The ROM 152 stores a program used by the MPU 150, control data such as operation parameters, and the like. The RAM 154 temporarily stores, for example, a program executed by the MPU 150.

The recording medium 156 functions as a storage unit (not illustrated), and stores various data, for example, data related to the detection method according to the present embodiment such as data indicating a pulse rate, or various kinds of applications. Here, examples of the recording medium 156 include a magnetic recording medium such as a hard disk and a non-volatile memory such as a flash memory. The recording medium 156 may be removably attached to the detection apparatus 100.

The communication interface 158 is a communication device included in the detection apparatus 100 and functions as a communication unit (not illustrated) that performs communication with an external apparatus in a wireless or wired manner via a network (or directly). Here, examples of the communication interface 158 include a communication antenna and a radio frequency (RF) circuit (wireless communication), an IEEE 802.15.1 port and a transceiving circuit (wireless communication), an IEEE 802.11 port and a transceiving circuit (wireless communication), and a local area network (LAN) terminal and a transceiving circuit (wired communication).

The input/output interface 160 connects, for example, the operation input device 162 and the display device 164. The operation input device 162 functions as the operation unit (not illustrated), and the display device 164 functions as the display unit (not illustrated). Here, examples of the input/output interface 160 include a Universal Serial Bus (USB) terminal, a digital visual interface (DVI) terminal, a high-definition multimedia interface (HDMI) (registered trademark) terminal, and various kinds of processing circuits.

For example, the operation input device 162 is arranged on the detection apparatus 100 and connected with the input/output interface 160 in the detection apparatus 100. Examples of the operation input device 162 include a button, a direction key, a rotational selector such as a jog dial, and a combination thereof.

For example, the display device 164 is arranged on the detection apparatus 100 and connected with the input/output interface 160 in the detection apparatus 100. Examples of the display device 164 include a liquid crystal display (LCD) and an organic EL display (also called an organic electroluminescence display or an organic light emitting diode display (OLED display)).

It will be appreciated that the input/output interface 160 can be connected with an external device such as an external operation input device of the detection apparatus 100 (for example, a keyboard, a mouse, or the like) or an external display device. The display device 164 may be, for example, a device on which display and a user operation can be performed such as the touch panel.

The heartbeat sensor 166 is a first detection device included in the detection apparatus 100, and functions as the first sensor unit 102. The heartbeat sensor 166 includes, for example, a plurality of electrodes and a processing circuit, and detects the first detection signal according to a potential difference between a plurality of electrodes.

The pulse wave sensor 168 is a second detection device included in the detection apparatus 100, and functions as the second sensor unit 104. The pulse wave sensor 168 includes, for example, a light source, a photodiode, and a processing circuit, and detects the second detection signal.

The motion sensor 170 is a third detection device included in the detection apparatus 100, and detects a motion of the detection apparatus 100. For example, in the case where the detection apparatus 100 is a wearable apparatus as illustrated in FIG. 2, the motion that the motion sensor 170 detects corresponds to a motion of the detection target wearing the detection apparatus 100.

The detection apparatus 100 performs the processing related to the detection method according to the present embodiment through the configuration illustrated in FIG. 9, for example. Note that the hardware configuration of the detection apparatus 100 according to the present embodiment is not limited to the configuration illustrated in FIG. 9.

For example, in the case of performing detection processing on the basis of the first detection signal acquired from an external heartbeat sensor connected thereto, the detection apparatus 100 need not include the heartbeat sensor 166.

For example, in the case of performing detection processing on the basis of the second detection signal acquired from an external pulse wave sensor connected thereto, the detection apparatus 100 need not include the pulse wave sensor 168.

For example, the detection apparatus 100 can have a configuration not including one or more of the recording medium 156, the communication interface 158, the operation input device 162, the display device 164, and the motion sensor 170.

Moreover, the detection apparatus 100 can have, for example, a configuration according to an application example of the detection apparatus 100, which is described later.

For example, a part or all of the configuration illustrated in FIG. 9 (or a configuration according to a modified example) may be implemented by one or more integrated circuits (ICs).

The example of the configuration of the detection apparatus 100 will be described with reference back to FIG. 8. The first sensor unit 102 is configured with the heartbeat sensor 166, and detects the first detection signal.

The second sensor unit 104 is configured with the pulse wave sensor 168, and detects the second detection signal.

The control unit 106 is configured with, for example, an MPU or the like and undertakes a role of controlling the detection apparatus 100 in general. The control unit 106 includes, for example, the processing unit 110 and undertakes a role of initiatively performing the processing related to the detection method according to the present embodiment.

The processing unit 110 undertakes a role of initiatively performing the processing related to the detection method according to the present embodiment.

For example, the processing unit 110 performs detection processing according to the present embodiment, and detects a pulse of the detection target on the basis of the first detection signal and the second detection signal. Furthermore, the processing unit 110 may calculate a pulse rate of the detection target on the basis of the detected pulse of the detection target.

The processing unit 110 may further perform, for example, either or both of display control processing and recording control processing.

The detection apparatus 100 performs the processing related to the detection method according to the present embodiment (for example, "detection processing" or "detection processing and either or both of display control processing and recording control processing") through, for example, the configuration illustrated in FIG. 8. Thus, the detection apparatus 100 can shorten time taken for detection of a pulse of the detection target through, for example, the configuration illustrated in FIG. 8.

Further, the detection apparatus 100 can have an effect obtained by performing the processing related to the detection method according to the present embodiment through, for example, the configuration illustrated in FIG. 8.

The configuration of the detection apparatus according to the present embodiment is not limited to the configuration illustrated in FIG. 8.

For example, in the detection apparatus according to the present embodiment, the processing unit 110 illustrated in FIG. 8 may be arranged separately from the control unit 106 (for example, may be implemented by a separate processing circuit). The processing unit 110 may be implemented by a plurality of processing circuits, and the function of the processing unit 110 may be distributedly performed by a plurality of processing circuits.

The configuration for implementing the processing related to the detection method according to the present embodiment is not limited to the configuration illustrated in FIG. 8, and a configuration according to a division form of the processing related to the detection method according to the present embodiment may be employed.

In the case of performing detection processing on the basis of the first detection signal acquired from an external heartbeat sensor, for example, the detection apparatus according to the present embodiment need not include the first sensor unit 102.

In the case of performing detection processing on the basis of the second detection signal acquired from an external pulse wave sensor, for example, the detection apparatus according to the present embodiment need not include the second sensor unit 104.

The detection apparatus has been described as the present embodiment, but the present embodiment is not limited to this example. For example, the present embodiment can be applied to various devices capable of performing the processing related to the detection method according to the present embodiment such as "any wearable apparatus used in a state in which it is worn on the body of the user such as an eyeware type apparatus," a "clock type apparatus," or a "wristlet type apparatus," a "computer such as a personal computer (PC)," a "communication apparatus such as a smart phone," a "tablet type apparatus," an "imaging apparatus such as a digital video camera or a digital still camera," a "game machine," and a "mobile object such as an automobile." For example, the present embodiment can be applied to a processing IC that can be incorporated into the above devices.

(Program According to Present Embodiment)

Time taken for detection of a pulse of the detection target can be shortened by executing a program causing a computer to function as the detection apparatus according to the present embodiment (for example, a program capable of executing the processing related to the detection method according to the present embodiment such as "detection processing" or "detection processing and either or both of display control processing and recording control processing") through a processor or the like in the computer.

Further, it is possible to obtain the effect obtained by the processing related to the detection method according to the present embodiment by executing a program causing a computer to function as the detection apparatus according to the present embodiment through a processor or the like in the computer.

It should be understood by those skilled in the art that various modifications, combinations, sub-combinations and alterations may occur depending on design requirements and other factors insofar as they are within the scope of the appended claims or the equivalents thereof.

For example, the example in which the program (computer program) causing the computer to function as the detection apparatus according to the present embodiment is provided has been described, but in the present embodiment, a recording medium including the program stored therein may also be provided.

The above configurations are examples of the present embodiment and understood to be included in the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A Detection Apparatus Including:

a heartbeat sensor that includes a plurality of electrodes and is configured to detect a first detection signal indicating heartbeat of a detection target via the plurality of electrodes;

a pulse wave sensor configured to detect a second detection signal indicating a pulse wave of the detection target; and a processing unit configured to detect a pulse of the detection target on the basis of the first detection signal and the second detection signal.

(2) The detection apparatus according to (1), wherein detection of the first detection signal in the heartbeat sensor is performed in conjunction with detection of the second detection signal in the pulse wave sensor.

(3) The detection apparatus according to (2), wherein the plurality of electrodes of the heartbeat sensor function as switches for detection start in the pulse wave sensor.

(4) The detection apparatus according to any one of (1) to (3), wherein the processing unit calculates a heart rate on the basis of the first detection signal, performs frequency analysis on the second detection signal, and detects a pulse of the detection target from a result of the frequency analysis, on the basis of a frequency of heartbeat calculated from the calculated heart rate.

(5) The detection apparatus according to (4), wherein the processing unit further detects a pulse of the detection target from a result of the frequency analysis, on the basis of a frequency corresponding to the pulse detected on the basis of the frequency of the heartbeat.

(6) The detection apparatus according to any one of (1) to (5), wherein the processing unit calculates a pulse rate of the detection target on the basis of the detected pulse of the detection target.

(7) The detection apparatus according to (6), wherein the processing unit causes the calculated pulse rate of the detection target to be displayed on a display screen.

(8) The detection apparatus according to (6) or (7), wherein the processing unit causes the calculated pulse rate of the detection target to be recorded on a recording medium.

(9) A detection method executed by a detection apparatus, including:
  detecting a pulse of a detection target, on the basis of a first detection signal that is acquired from a heartbeat sensor including a plurality of electrodes and indicates heartbeat of the detection target, and a second detection signal that is acquired from a pulse wave sensor and indicates a pulse wave of the detection target.

(10) A program causing a computer to implement a function of:
  detecting a pulse of a detection target, on the basis of a first detection signal that is acquired from a heartbeat sensor including a plurality of electrodes and indicates heartbeat of the detection target, and a second detection signal that is acquired from a pulse wave sensor and indicates a pulse wave of the detection target.

What is claimed is:

1. A detection apparatus comprising:
   a heartbeat sensor that includes a plurality of electrodes and is configured to detect a first detection signal indicating heartbeat of a detection target via the plurality of electrodes;
   a pulse wave sensor configured to detect a second detection signal indicating a pulse wave of the detection target, wherein the plurality of electrodes of the heartbeat sensor function as switches for detection start in the heartbeat sensor and the pulse wave sensor; and
   circuitry configured to
      determine whether a potential difference between the plurality of electrodes is detected for longer than a predetermined period of time;
      start operation of the pulse wave sensor when it is determined that the potential difference between the plurality of electrodes is detected for longer than the predetermined period of time;
      calculate a frequency of a heartbeat from the first detection signal;
      set a frequency range based on the frequency of the heartbeat calculated from the first detection signal as a frequency range for detecting the pulse wave from the second detection signal; and
      continuously calculate the heart rate based on the pulse wave detected from the second detection signal.

2. The detection apparatus according to claim 1, wherein detection of the first detection signal in the heartbeat sensor is performed in conjunction with detection of the second detection signal in the pulse wave sensor.

3. The detection apparatus according to claim 1, wherein the circuitry is configured to
   perform frequency analysis on the second detection signal, and
   detect a pulse of the detection target from a result of the frequency analysis, on the basis of the frequency range set based on the frequency of the heartbeat calculated from the first detection signal.

4. The detection apparatus according to claim 3, wherein the circuitry is further configured to detect the pulse of the detection target from the result of the frequency analysis, on the basis of a frequency corresponding to the pulse detected on the basis of the frequency of the heartbeat.

5. The detection apparatus according to claim 3, wherein the circuitry is configured to calculate a pulse rate of the detection target on the basis of the detected pulse of the detection target.

6. The detection apparatus according to claim 5, wherein the circuitry is configured to cause the calculated pulse rate of the detection target to be displayed on a display screen.

7. The detection apparatus according to claim 5, wherein the circuitry is configured to cause the calculated pulse rate of the detection target to be recorded on a recording medium.

8. The detection apparatus of claim 1, wherein the circuitry is configured to:
   determine whether a living body is in contact with at least one of the plurality of electrodes; and
   start operation of the pulse wave sensor when it is determined that the living body is in contact with the at least one of the plurality of electrodes.

9. The detection apparatus according to claim 1, wherein the heartbeat sensor includes at least a first electrode, a second electrode and a third electrode.

10. The detection apparatus according to claim 1, wherein the detection apparatus is a clock-type wearable apparatus configured to be worn on the detection target's arm.

11. The detection apparatus of claim 10, wherein the heartbeat sensor comprises:
    a first electrode positioned on a front face of the clock-type wearable apparatus, and
    a second electrode provided on a back surface of the clock-type wearable apparatus that faces the detection target's arm when the clock-type wearable apparatus is worn by the detection target.

12. The detection apparatus of claim 11, wherein the heartbeat sensor includes a third electrode position on the front face of the clock-type wearable apparatus.

13. The detection apparatus of claim 12, wherein the circuitry is configured to initiate detection start by the heartbeat sensor and the pulse wave sensor upon detecting a touch input to at least one of the first electrode and the third electrode.

14. The detection apparatus of claim 13, wherein the circuitry is configured to output a notification to the detection target that the circuitry is calculating the heart rate based on the pulse wave detected from the second detection signal while the touch input to the at least one of the first electrode and the third electrode is detected.

15. The detection apparatus of claim 14, wherein the circuitry is configured to continuously calculate the heart rate based on the pulse wave detected from the second detection signal when the touch input to the at least one of the first electrode and the third electrode is no longer detected.

16. A detection method executed by a detection apparatus, comprising:

receiving, into circuitry, a first detection signal that is acquired from a heartbeat sensor including a plurality of electrodes and indicates heartbeat of the detection target;

receiving, into the circuitry, a second detection signal that is acquired from a pulse wave sensor and indicates a pulse wave of the detection target, wherein the plurality of electrodes of the heartbeat sensor function as switches for detection start in the heartbeat sensor and the pulse wave sensor;

determining, using the circuitry, whether a potential difference between the plurality of electrodes is detected for longer than a predetermined period of time;

starting, by the circuitry, operation of the pulse wave sensor when it is determined that the potential difference between the plurality of electrodes is detected for longer than the predetermined period of time;

calculating, using the circuitry, a frequency of a heartbeat from the first detection signal;

setting, using the circuitry, a frequency range based on the frequency of the heartbeat calculated from the first detection signal as a frequency range for detecting the pulse wave from the second detection signal; and continuously calculating, using the circuitry, the heart rate based on the pulse wave detected from the second detection signal.

17. A non-transitory, computer-readable medium storing instructions that, when executed on a computer, cause the computer to implement a function of:

receiving a first detection signal that is acquired from a heartbeat sensor including a plurality of electrodes and indicates heartbeat of the detection target;

receiving a second detection signal that is acquired from a pulse wave sensor and indicates a pulse wave of the detection target, wherein the plurality of electrodes of the heartbeat sensor function as switches for detection start in the heartbeat sensor and the pulse wave sensor;

determining whether a potential difference between the plurality of electrodes is detected for longer than a predetermined period of time;

starting operation of the pulse wave sensor when it is determined that the potential difference between the plurality of electrodes is detected for longer than the predetermined period of time;

calculating a frequency of a heartbeat from the first detection signal;

setting a frequency range based on the frequency of the heartbeat calculated from the first detection signal as a frequency range for detecting the pulse wave from the second detection signal; and continuously calculating the heart rate based on the pulse wave detected from the second detection signal.

* * * * *